US009002463B2

(12) United States Patent
    Tiedtke

(10) Patent No.: US 9,002,463 B2
(45) Date of Patent: Apr. 7, 2015

(54) RETINAL IMPLANT WITH RECTIFIED AC POWERED PHOTODIODE

(75) Inventor: Hans-Jürgen Tiedtke, Bonn (DE)

(73) Assignee: Pixium Vision SA, Paris (FR)

( * ) Notice: Subject to any disclaimer, the term of this patent is extended or adjusted under 35 U.S.C. 154(b) by 584 days.

(21) Appl. No.: 12/811,813

(22) PCT Filed: Jan. 14, 2009

(86) PCT No.: PCT/EP2009/000176
    § 371 (c)(1),
    (2), (4) Date: Sep. 22, 2010

(87) PCT Pub. No.: WO2009/090047
    PCT Pub. Date: Jul. 23, 2009

(65) Prior Publication Data
    US 2011/0009959 A1    Jan. 13, 2011

(30) Foreign Application Priority Data
    Jan. 14, 2008    (WO) .................. PCT/EP2008/000231

(51) Int. Cl.
    *A61N 1/05*    (2006.01)
    *A61N 1/36*    (2006.01)
    *A61N 1/02*    (2006.01)

(52) U.S. Cl.
    CPC ............ *A61N 1/36046* (2013.01); *A61N 1/025* (2013.01); *A61N 1/0543* (2013.01)

(58) Field of Classification Search
    CPC ..................... A61N 1/0543; A61N 1/36046
    USPC ....................................... 607/53, 54
    See application file for complete search history.

(56) References Cited

U.S. PATENT DOCUMENTS 4,628,933 A * 12/1986 Michelson .................. 607/53
6,400,989 B1    6/2002 Eckmiller
(Continued)

FOREIGN PATENT DOCUMENTS

| EP | 0 247 649 | 12/1987 |
| JP | 2003152649 | 5/2003 |
| JP | 2006155345 | 6/2006 |

(Continued)

OTHER PUBLICATIONS

Palanker et al., "Design of a high-resolution optoelectronic retinal prosthesis", J. Neural Eng. 2 (2005) S105-S120.

*Primary Examiner* — Eric D. Bertram
(74) *Attorney, Agent, or Firm* — Workman Nydegger

(57) ABSTRACT

The present invention relates to a microelectronics element, such as an optical receiver element, for a medical implant device to be implanted in the human or animal body, particularly for a retinal implant device. The microelectronics element comprises a functional unit including application specific microelectronics, such as a photodiode, for performing a function in the medical implant device, and rectifier means adapted for converting an AC supply voltage into a DC voltage. The DC voltage provided by the rectifier means, or an operating voltage derived from the DC voltage, is configured to be supplied to the functional unit. Further, the functional unit and the rectifier means are integrated on a common semiconductor substrate and configured such that the rectifier means isolates the microelectronics element from application of an external DC supply voltage. The invention also relates to a medical implant device, such as a retinal implant, which incorporates such a microelectronics element.

19 Claims, 5 Drawing Sheets

(56) References Cited

U.S. PATENT DOCUMENTS

2003/0158588 A1 8/2003 Rizzo et al.
2004/0117011 A1 6/2004 Aharoni et al.
2004/0186533 A1* 9/2004 Greenberg et al. ............ 607/54
2007/0142877 A1 6/2007 McLean

FOREIGN PATENT DOCUMENTS

| WO | WO 99/45870 | 9/1999 |
| WO | WO 03/061537 | 7/2003 |
| WO | WO2007006376 | 1/2007 |
| WO | WO 2007/130686 | 11/2007 |

* cited by examiner

US 9,002,463 B2

RETINAL IMPLANT WITH RECTIFIED AC POWERED PHOTODIODE

CROSS-REFERENCE TO RELATED APPLICATIONS

This application is a U.S. Nationalization of PCT International Application No. PCT/EP2009/000176 filed 14 Jan. 2009, entitled "RETINAL IMPLANT WITH RECTIFIED AC POWERED PHOTODIODE," which claims the benefit of PCT International Application No. PCT/EP2008/000231 filed 14 Jan. 2008, entitled "OPTICAL RECEIVER ELEMENT" the entireties of which are incorporated herein by reference.

TECHNICAL FIELD

The present invention relates to a medical implant device, and more particularly to a microelectronics element, such as a microchip, to be incorporated in the medical implant device.

In a particularly preferred application of the present invention, the medical implant device comprises a retinal implant and the microelectronics element may be in the form of an optical receiver element for the retinal implant. It will be appreciated, however, that the present invention is not limited to this particular application, but may be employed in various medical implant applications where microelectronic components are used, including, for example, pacemakers, cochlea implants and hearing aids, neural implants, as well as other implant devices.

BACKGROUND TO THE INVENTION

When microelectronic components are employed in medical implant devices, an important consideration is to protect the microelectronic components from the adverse affects of the aqueous environment usually encountered within the human or animal body. In particular, the moisture or fluids of the human or animal body to which such medical implant devices are almost invariably exposed are typically electrolytic conductors and create a potentially corrosive environment for the microelectronic components, especially when those components are supplied with a direct current (DC) voltage via a battery power source or a converted alternating current (AC) power supply. When the microelectronic components are exposed to corrosive influences, the efficacy of the medical implant device can be compromised leading to reduced performance or even to a complete failure of the device. For example, when an optical receiver element is used in an environment where it is exposed to aqueous solutions or other liquids, proper functioning of the receiver element may be impaired by electrochemical corrosion.

A typical solution to this problem is to enclose or encase the microelectronics and other sensitive components in such a way that they are impervious to moisture. For example, the sensitive components or even the entire medical implant device may be hermetically sealed from the aqueous environment of the body, for example, by an enclosure or a coating layer, such as a polymer coating. Silicone polymers are particularly favorable in this context because of their high biocompatibility. Such a coating layer, however, not only complicates the manufacturing process, but also has the problem that the microelectronic components still need to maintain an electrical contact with external components. This often requires that a physical connection be provided through the protective enclosure or coating layer and, thus, a breach in the protective enclosure or layer is created. Additionally, while sealing some components or the entire implant device with, for example, a polymer coating layer can provide effective protection from a corrosive environment, it can also involve a conflict between the requirements of impermeability to moisture on the one hand, and flexibility of the implant device on the other, particularly in the field of retinal implants.

SUMMARY OF THE INVENTION

It is therefore an object of the present invention to provide a medical implant device in which the sensitive microelectronic components of the device are adequately protected from the aqueous environment of the human or animal body, without all of the drawbacks or limitations noted above.

The present invention provides a microelectronics element for a medical implant device as. In this respect, the present invention is preferably embodied as an optical receiver element. Furthermore, the invention provides a medical implant device, such as a retinal implant. In one broad aspect, therefore, the present invention provides a microelectronics element, such as a microchip, for a medical implant device to be implanted in the human or animal body, the microelectronics element comprising: a functional unit including application specific microelectronics for performing a function in the medical implant device, and rectifier means adapted for converting an alternating current (AC) supply voltage into a direct current (DC) voltage. The DC voltage provided by the rectifier means, or an operating voltage which is derived from the DC voltage, is configured to be supplied to the functional unit. The functional unit and the rectifier means are integrated on a common semiconductor substrate such that the microelectronics element does not need an external DC voltage supply. In other words, the microelectronics element of the invention is configured to avoid, or to be isolated from, application of a DC signal; for example, there is no DC signal at an outer region of the microelectronics element (i.e. microchip) that forms an interface with an aqueous environment in the human or animal body.

Thus, the present invention provides corrosion suppression means adapted to isolate a microelectronics element or a microchip from the adverse affects of an externally applied or acting DC voltage. In particular, the configuration of the microelectronics element or microchip of the invention renders it designed for exposure to an AC supply voltage only, and desirably excludes the flow of direct current outside of, out from, and/or at a body-interface of the element or microchip of the invention. This, in turn, renders the microelectronics element or microchip inherently resistant to the corrosive effects of the aqueous environment within the body. In particular, the external application of an AC supply voltage to the microelectronics element or microchip of the invention does not give rise to the same corrosive effects experienced with DC voltage supply due to the constantly (and frequently) alternating polarity of the voltage supply. The integration of the rectifier means with the application specific microelectronics of the functional unit on one common semiconductor substrate, e.g. in a microchip, in such a manner that the rectifier means isolates the microelectronics element from an externally applied or acting DC voltage thus forms a corrosion suppression means in the microelectronics element. While a polymer coating layer may still be desirably employed with such an element, lower thicknesses of the coating layer providing greater flexibility are more viable.

In a preferred form of the invention, the microelectronics element further comprises a capacitor integrated on the common substrate and connected to a terminal of said functional unit, such that the capacitor is adapted for decoupling an alternating component of a signal output from the functional unit. In particular, the decoupling capacitor may be arranged to ensure that a signal output from the microelectronics element or microchip (e.g. at an output pin) only has an alternating component. This capacitor arrangement can therefore again serve to exclude the direct action of an external DC signal on an outside of the microelectronics element or microchip (i.e. at an interface with an aqueous environment of the body); that is, it may serve to avoid direct exposure of the microelectronics element or microchip of the invention to an external DC signal.

In a preferred form of the invention, the microelectronics element further comprises an amplifier adapted to amplify a signal which is output from the functional unit, or a signal which is derived therefrom.

In one particular form of the invention, the application specific microelectronics of the functional unit may comprise a processor, such as a data processor.

In a more preferred form of the invention, however, the functional unit consists of, or comprises, a photosensor which is adapted for detecting incident light, such that the microelectronics element can be embodied as an optical receiver element. The photosensor may, for example, be adapted for converting a modulated light signal into a corresponding detection signal. In this connection, the photosensor may be adapted to receive and detect a light signal, and more preferably, an infrared light signal. The photosensor may, for example, be in the form of a photodiode.

In a particularly preferred embodiment, therefore, the invention provides an optical receiver element comprising: a photosensor adapted for detecting incident light, and a rectifier adapted for converting an AC supply voltage into a DC voltage. The DC voltage from the rectifier, or an operating voltage derived from the DC voltage, is supplied to the photosensor, and the rectifier and the photosensor are integrated on one common semiconductor substrate.

By integrating the rectifier and the photodiode on one common substrate, the optical receiver element is adapted to be operated with AC voltage instead of DC voltage. Photodiodes used previously have typically required a DC voltage supply, which has often led to the galvanic corrosion of metal elements that are exposed to an aqueous environment. In the optical receiver element according to embodiments of the present invention, the DC voltage supply is replaced by an AC voltage supply. Thus, the DC voltage generated by the rectifier does not come into direct contact with the medium external to the optical receiver element. With regard to the AC supply voltage, the problems related to galvanic corrosion are much less severe, because the polarity of the supply lines changes at high frequency. By employing an AC voltage as a supply voltage, therefore, damage due to galvanic corrosion may be significantly reduced or even completely avoided. This invention thus supports the use of optical data transmission in environments where galvanic corrosion is likely to occur.

Optical data transmission via modulated light, preferably in the infrared spectrum, offers a multitude of advantages. Optical data transmission is characterized by its resistance to interference. The design of the transmitter and the receiver element is comparatively simple. Furthermore, the amount of energy consumed by the optical receiver element is quite low, and the area needed for accommodating an optical receiver element is relatively small.

In another broad aspect, the invention provides a microelectronics element, such as a microchip, for a medical implant device to be implanted in the human or animal body, the microelectronics element comprising: a functional unit including application specific microelectronics for performing a function in the medical implant device, rectifier means adapted for converting an AC supply voltage into a DC voltage, and corrosion suppression means for inhibiting electrolytic corrosion of the microelectronics element in an aqueous environment. The DC voltage provided by the rectifier means, or an operating voltage which is derived from the DC voltage, is configured to be supplied to the functional unit. The corrosion suppression means comprises a circuit configuration in which the functional unit and the rectifier means are integrated on a common semiconductor substrate such that the microelectronics element avoids the presence of an external DC signal being (directly) applied to and/or acting (directly) on the microelectronics element.

In this way, even where a physical electrical connection extends through a thin coating layer in the microelectronics element or microchip of the invention, the isolation of the element or microchip from a DC signal by the corrosion suppression means results in the desired inhibition of any corrosive effects. That is, the microelectronics element or microchip of the invention is not exposed to direct current in the corrosive aqueous environment.

A medical implant according to an embodiment of the present invention comprises a microelectronics element, preferably in the form of an optical receiver element, as described above. The medical implant is desirably a retinal implant, with the optical receiver element being adapted for receiving and detecting a modulated light signal.

The microelectronics element of the invention is especially well-suited for use in a medical implant device that is exposed to all kinds of body fluids. For a medical implant, long-term stability is highly important, because replacement of an implant device typically requires surgery. By using a microelectronics element according to an embodiment of the present invention, electrochemical corrosion is significantly reduced or even completely eliminated, and hence, the lifetime of the medical implant device is prolonged. By using an AC supply voltage for microelectronics elements (e.g. optical receiver elements) that have to date generally been supplied by a DC voltage, the long-term stability of the medical implant device is improved.

BRIEF DESCRIPTION OF THE DRAWINGS

The above and further features and advantages of the present invention will become more apparent from the following detailed description of preferred embodiments of the invention with reference to the accompanying drawings, in which like reference numerals identify like parts, and in which.

DETAILED DESCRIPTION OF THE PREFERRED EMBODIMENTS

Figure 1:
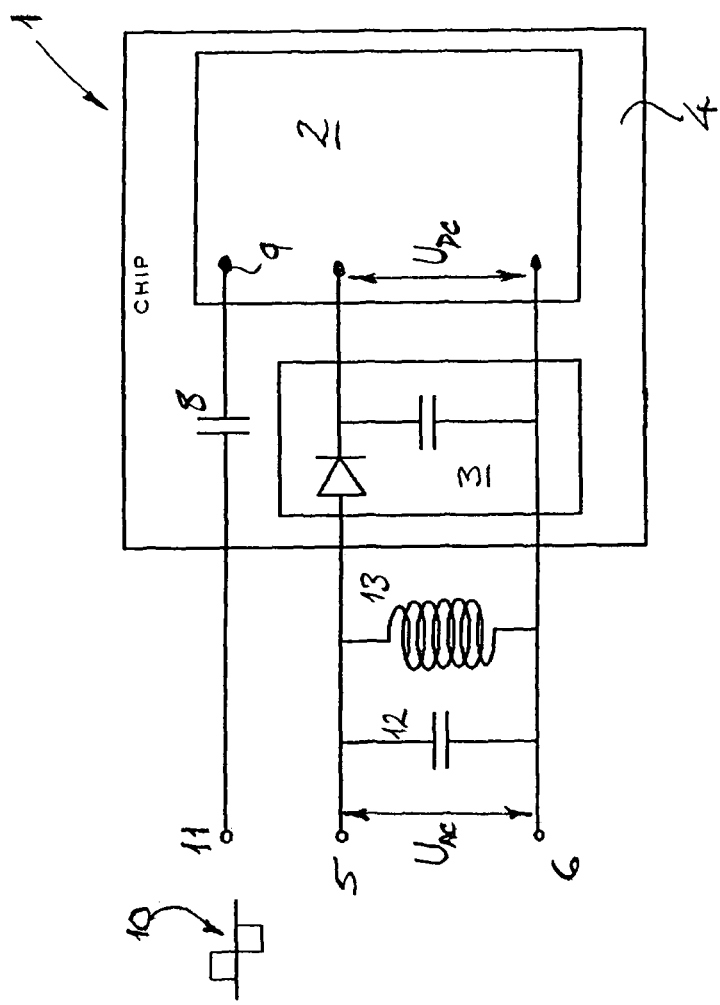
FIG. 1 shows a microelectronics element illustrating an example of the concept of the present invention.

Referring firstly to FIG. 1 of the drawings, a microelectronics element in the form of a microchip 1 illustrating an example of the invention is shown. The microchip 1 is designed to be implanted in the human or animal body in a medical implant device and comprises application specific microelectronics in a functional unit 2 for performing a function in the medical implant device, and rectifier means 3 adapted for converting an AC supply voltage into a DC voltage. In this example, the rectifier means 3 comprises at least one diode and may include one or more filter capacitor or buffer capacitor for generating a smoothed DC voltage. It will be appreciated, however, that the rectifier means 3 may take a variety of different forms (e.g. a diode bridge-type rectifier, a voltage-adjusting rectifier, etc.) and may comprise an active rectifier circuit or a passive rectifier circuit.

Both the functional unit 2 and the rectifier means 3 are integrated on a common semiconductor substrate 4 (formed, for example, from silicon, germanium or any other suitable material), with the arrangement of the rectifier means 3 and the associated circuitry configured to form corrosion suppression means with which the microelectronics element, i.e. the microchip 1, avoids any externally applied or acting DC signal or DC supply voltage. In other words, the microchip 1 is adapted to be driven by an AC voltage supply $U_{AC}$ which is applied to voltage supply pins 5 and 6. The frequency of the AC voltage preferably lies in the range of about 100 kHz to 100 MHz. The rectifier means 3 is adapted to convert the AC voltage supply $U_{AC}$ applied to the voltage supply pins 5 and 6 into a DC voltage $U_{DC}$ and this DC voltage then forms a supply voltage for the application specific microelectronics of the functional unit 2, i.e. at one or more input terminal of the functional unit 2. The microchip 1 further comprises a capacitor 8, which is connected to an output terminal 9 of the functional unit 2. The capacitor 8 is adapted for decoupling an output signal 10 from the functional unit 2, such that an output signal 10 at an output pin 11 of the microchip 1 comprises the alternating component of the signal generated by or output from the functional unit 2. A tuning arrangement comprising a capacitor 12 and an inductor 13 may optionally be provided in the AC voltage supply circuitry between the supply pins 5, 6. Although not so shown, it will be appreciated that the tuning capacitor 12 and/or inductor 13 could also be integrated on the common semiconductor substrate 4.

Figures 2, 3:
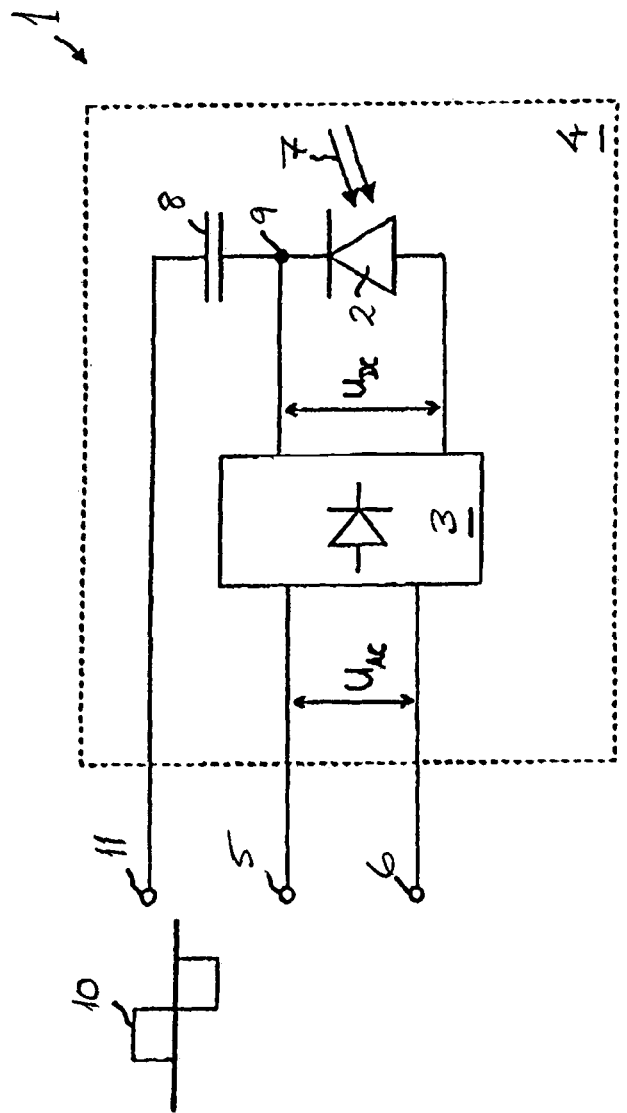
FIG. 2 shows an optical receiver element according to an embodiment of the present invention.
FIG. 3 shows the packaging of an optical receiver element according to an embodiment of the present invention.

With reference now to FIG. 2 of the drawings, a microelectronics element embodied as an optical receiver element 1 according to the present invention is shown. This embodiment basically corresponds to the example in FIG. 1, with the optical receiver element 1 comprising a functional unit 2, this time in the form of a photosensor comprising a photodiode. The optical receiver element 1 further comprises a rectifier 3, and both the photodiode 2 and the rectifier 3 are integrated on a common semiconductor substrate 4. As before, the rectifier can have a variety of different forms (e.g. a diode bridge-type rectifier, a voltage-adjusting rectifier, etc.) and may comprise an active rectifier circuit or a passive rectifier circuit. Also, as the semiconductor material, silicon, germanium or any other suitable material may be again used. In this case, however, the proper choice of the semiconductor material will usually depend upon the desired range of the wavelengths of the light to be detected by the photodiode 2. For wavelengths of up to 1.1 micrometer, for example, silicon is usually a more suitable material, whereas for wavelengths of up to 1.8 micrometer germanium may be used.

The optical receiver element 1 is driven by an AC voltage $U_{AC}$. Preferably, the frequency of the AC voltage lies between 100 kHz to 100 MHz. The AC voltage $U_{AC}$ is applied to the voltage supply pins 5 and 6. The rectifier 3 is adapted for converting the AC voltage into a DC voltage $U_{DC}$. The rectifier 3 is composed of one or more diodes and may comprise one or more filter capacitors or buffer capacitors for generating a smoothed DC voltage $U_{DC}$. This DC voltage then forms a supply voltage for the photodiode 2. The photodiode 2 is used in the so-called "photoconductive mode" under reverse bias. Photodiodes which are operated in the photoconductive mode are more sensitive to light than the ones based upon the photovoltaic effect and also tend to have lower capacitance, which improves the speed of their time response. A further effect of the reverse bias is widening of the depletion layer and strengthening of the photocurrent.

When a beam of modulated light 7 is incident on the photodiode 2, a photocurrent is generated that alternates in accordance with the modulation of the modulated light 7. The optical receiver element 1 in this embodiment of the invention also comprises a capacitor 8 connected to a terminal 9 of the photodiode 2, with the capacitor 8 adapted for uncoupling or decoupling an output signal 10 from the photodiode circuit. The output signal 10 solely comprises the alternating component of the received signal. The modulation of the modulated light 7 may, for example, be chosen such that the output signal 10 does not comprise any constant component, or only a negligible constant component. The output signal 10 is supplied to an output pin 11 of the optical receiver element 1.

FIG. 3 of the drawings schematically illustrates the external design of the optical receiver element 1. In this regard, the optical receiver element 1 comprises a photosensitive area 15 that is made of a material that is transparent for the light to be detected. Preferably, the voltage supply pins 5, 6 and the output pin 11 are located at a reverse side of the packaged element 1 opposite to the photosensitive area 15.

The optical receiver element 1 shown in FIG. 2 and FIG. 3 is especially well-suited for realizing optical data transmission in a surrounding where electrochemical corrosion is likely to occur. By integrating the photodiode 2 and the rectifier 3 on one common substrate 4, the optical receiver element 1 is designed to be operated with AC voltage instead of DC voltage. Photodiodes that have been used to date have required a DC voltage supply, and this has often led to galvanic corrosion of the metal elements exposed to the aqueous environment in the body. In the optical receiver element 1 according to the present invention, however, the DC voltage supply is replaced by an AC voltage supply, so that damage resulting from galvanic corrosion may be significantly reduced or completely avoided. This allows use of optical data transmission in aqueous environments where galvanic corrosion was previously a problem.

As noted above, optical data transmission via modulated light, preferably in the infrared spectrum, offers numerous advantages. Firstly, optical data transmission is characterized by its resistance to interference. Further, the design of the transmitter and receiver elements is comparatively simple, and the amount of energy consumed by an optical receiver element is quite low. The area required to accommodate an optical receiver element is also relatively small.

Figure 4:
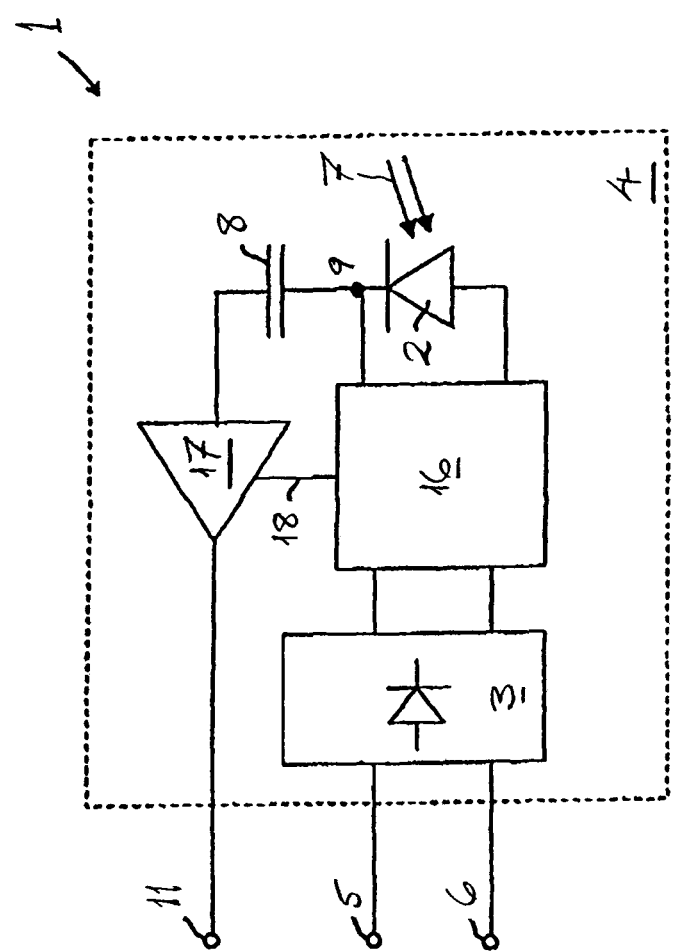
FIG. 4 shows an optical receiver element according to another embodiment of the present invention.

In FIG. 4 of the drawings another embodiment of an optical receiver element 1 according to the present invention is depicted. In this example, the optical receiver element 1 comprises a functional unit 2, again in the form of a photosensor comprising a photodiode, in combination with a rectifier 3, a capacitor 8, an ambient light control circuit 16, and an amplifier 17. All of these components are integrated on one common semiconductor substrate 4. Compared to the embodiment shown in FIG. 2 of the drawings, therefore, the ambient light control circuit 16 and the amplifier 17 have been added.

Again, an AC supply voltage $U_{AC}$ is applied to the two voltage supply pins 5, 6. The rectifier 3 is adapted for converting the AC supply voltage $U_{AC}$ to a DC voltage $U_{DC}$, with $U_{DC}$ then forming, or being used as, a supply voltage for the ambient light control circuit 16 and the amplifier 17. The ambient light control circuit 16 determines the intensity of the ambient light. Dependent upon the intensity of the ambient light, the ambient light control circuit 16 supplies an operating voltage to the photodiode 2, whereby the operating point of the photodiode 2 is set to a respective optimum. When modulated light 7 strikes the photodiode 2, a modulated photocurrent is generated. The alternating component of the photocurrent is uncoupled or decoupled by the capacitor 8 and supplied to the amplifier 17.

The ambient light control circuit 16 may comprise an automatic gain control. The automatic gain control is adapted for controlling the gain of the amplifier 17 in dependence upon the amplitude of the modulated detection signal, and for providing a gain control signal 18 to the amplifier 17. The amplifier's input signal is amplified according to the gain control signal 18, and the amplifier's output signal is provided to the output pin 11 of the optical receiver element 1. According to a preferred embodiment of the invention, amplification of the modulated detection signal is activated as soon as the ambient light intensity exceeds a predefined threshold. According to a further preferred embodiment, the amplifier 16 has a logarithmic characteristic.

Figure 5:
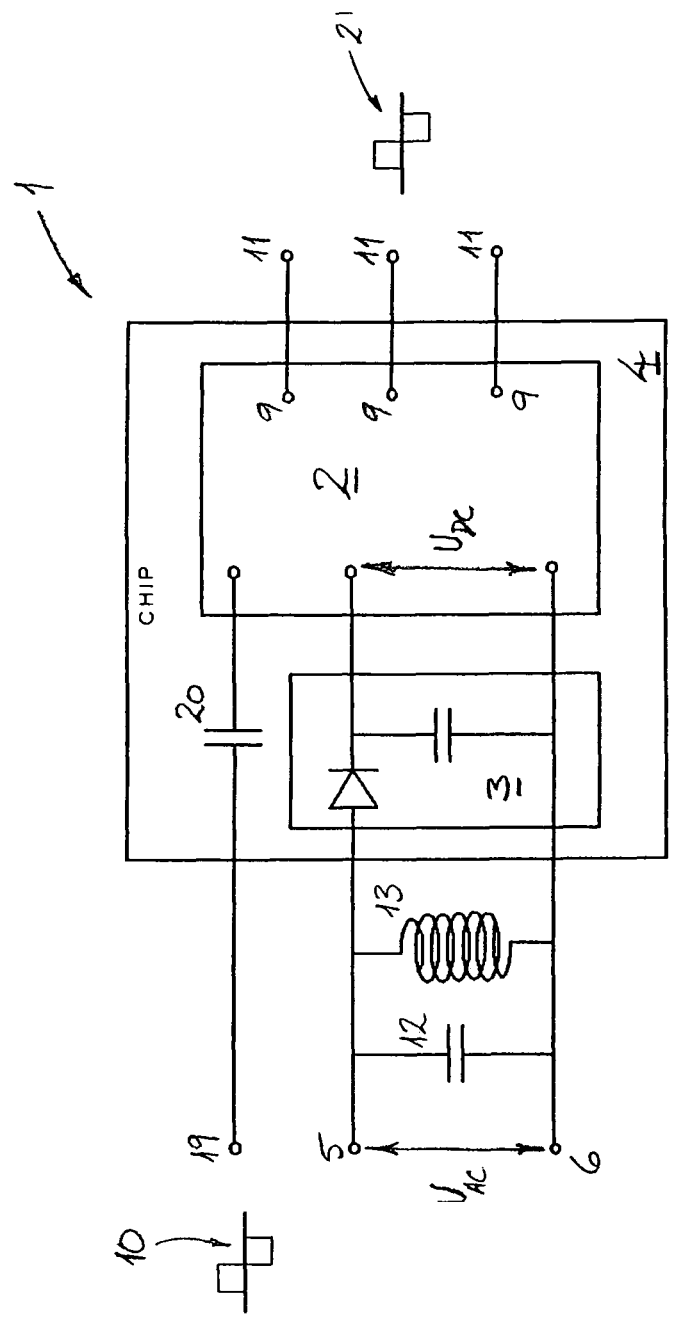
FIG. 5 shows a microelectronics element illustrating another example of the concept of the present invention.

With reference now to FIG. 5 of the drawings, a microelectronics element in the form of a microchip 1 illustrating another example of the invention is shown. The microchip 1 is again designed to be implanted in the human or animal body in a medical implant device and again comprises application specific microelectronics in a functional unit 2 for performing a function in the medical implant device, and rectifier means 3 adapted for converting an AC supply voltage into a DC voltage. As before, the rectifier means 3 comprises at least one diode and may include one or more filter capacitor or buffer capacitor for generating a smoothed DC voltage. In other words, the rectifier means 3 may again take a variety of different forms (e.g. a diode bridge-type rectifier, a voltage-adjusting rectifier, etc.) and may comprise an active rectifier circuit or a passive rectifier circuit. Importantly, both the functional unit 2 and the rectifier means 3 are again integrated on a common semiconductor substrate 4, with the arrangement of the rectifier means 3 and the associated circuitry configured to form a corrosion suppression means with which the microelectronics element, i.e. the microchip 1, avoids or is isolated from an externally applied or acting DC signal or DC supply voltage.

Thus, the microchip 1 in FIG. 5 is adapted to be driven by an AC voltage supply $U_{AC}$ which is applied to voltage supply pins 5 and 6. The rectifier means 3 is adapted to convert the AC voltage supply $U_{AC}$ applied to the voltage supply pins 5 and 6 into a DC voltage $U_{DC}$ and this DC voltage is then used to supply voltage to the application specific microelectronics of the functional unit 2. In contrast to the embodiments of FIGS. 1 to 4, however, in which an input interface of the microchip 1 (not illustrated in those cases) was, for example, adapted for optical data transfer, the microchip 1 in the present example comprises an input pin 19 for receiving a signal 10 to be processed. This signal 10 may, for example, be the output signal of an optical receiver element 1 according to one the embodiments of FIGS. 1 to 4. The capacitor 20 shown in the input line extending from the input terminal 19 is optional and may be included to filter or tune the signal 10.

In this case, therefore, the functional unit 2 of the microchip 1 may comprise a processor adapted for processing the output signal 10 from an optical receiver element 1. Thus, when employed in a retinal implant device, as will be described in more detail below, the microchip 1 of FIG. 5 may be adapted for processing the signal 10 in the processor unit 2 and then transmitting stimulation signals 21 to the plurality of electrodes of a retina-stimulating electrode array in the retinal implant via a plurality of output pins 11 of the microchip 1.

Figure 6:
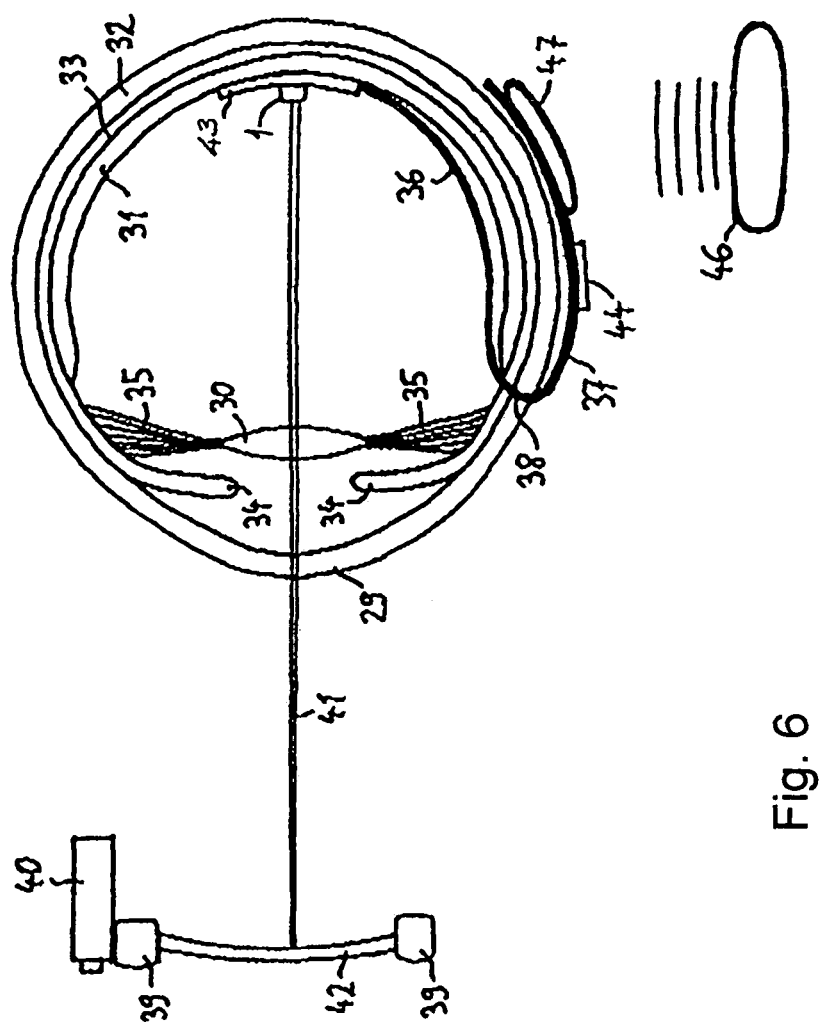
FIG. 6 shows a retinal implant device comprising an optical receiver element according to an embodiment of the present invention.

With reference now to FIG. 6 of the drawings, a retinal implant device for implantation in a patient's eye is shown. Light passing through the cornea 29 and the eye lens 30 (which may or may not be present in the patient to be treated) strikes the retina 31, which covers a large part of the eyeball's interior, primarily at the inner surface of the rear or posterior wall of the eye. The eyeball's outer surface is formed by the sclera 32. A choroid membrane 33 is located between the retina 31 and the sclera 32. The iris 34 determines the size of the pupil and, thus, the amount of light that may enter into the interior of the eye. The eye lens 30 is fixed by the ciliary muscle 35 or is explanted. The implant device comprises an intraocular part 36 and an extra-ocular part 37. The intraocular part 36 is located in the interior of the eye, whereas the extraocular part 37 is fixed to the outer surface of the sclera 32. The intraocular part 36 and the extraocular part 37 are electrically connected by a wire connection 38 that passes through the sclera 32 at a position directly behind the ciliary muscle 35.

A retinal implant device is a visual prosthesis designed to provide some degree of visual perception to patients suffering from retinal degenerative diseases such as retinitis pigmentosa or macula degeneration. To this end, the apparatus includes an eye glasses 42 to be worn by the patient, the eye glasses 42 having a small video camera 40 integrated in or on the glasses frame 39. A video signal acquired by the video camera 40 is processed, and the image data are transmitted to the retinal implant device 43 via a modulated infrared light beam 41. The infrared beam 41 may, for example, be generated by an infrared transmitter LED (not shown) located on or in the vicinity of the glasses 42. The modulated infrared beam 41 passes through the patient's eye, including through the lens 30 of the eye, if still present, or otherwise through the space normally occupied by the lens 30, and strikes an optical receiver element 1 of the invention incorporated in the implant device 43.

According to embodiments of the present invention, a microelectronics element in the form of an optical receiver element 1 of the kind described with reference to drawing FIGS. 3 to 5 may be employed, driven by an AC supply voltage. For a retinal implant, long-term stability is an important issue. Therefore, it is important to avoid galvanic corrosion of the wire connections and voltage supply lines. By supplying an AC supply voltage to the optical receiver element 1, galvanic corrosion can be either eliminated or at least significantly reduced.

The image data received by the optical receiver element 1 is forwarded via the wire connection 38 to a retina stimulation chip 44. The retina stimulation chip 44 is operative to convert the image data into a sequence of stimulation pulses. Preferably, the retinal stimulation chip 44 is implemented as a digital signal processing chip and may also constitute an embodiment of the present invention. That is, the retinal stimulation chip 44 may comprise a microchip incorporating the concept described above with reference to drawing FIG. 5, in which the functional unit comprises a processor circuit. Via the wire connection 38, the stimulation pulses are supplied to an array of micro-contacts located on the intraocular part 36, namely on the retinal implant 43 implanted directly on the retina 31. The micro-contacts are adapted for stimulating the ganglia cells of the retina 31.

The electrical power required for operating the retinal implant, in particular the electrical power consumed by the optical receiver element 1 and/or the retina stimulation chip 44, can be provided by a high frequency transmitter coil 46 that is inductively coupled with a high frequency receiver coil 47 located on the extra-ocular part 37 of the retina implant. The AC voltage provided by such a high frequency receiver coil 47 may thus used for powering either or both of the optical receiver element 1 and the retina stimulation chip 44.

The invention claimed is:

1. A retinal implant device configured to be implanted in a human or animal body, the retinal implant device comprising:
    a microelectronics element, the microelectronics element comprising:
        a functional unit including application specific microelectronics for performing a function in the medical implant device,
        rectifier means adapted for converting an AC supply voltage into a DC voltage,
        wherein the DC voltage provided by the rectifier means or an operating voltage derived from the DC voltage is adapted to be supplied to the functional unit,
        wherein the functional unit and the rectifier means are integrated on a common semiconductor substrate such that the micro-electronics element avoids an external DC supply voltage and a DC signal,
    wherein the retinal implant device comprises an intra-ocular implant configured to be located inside an eyeball and an extra-ocular implant configured to be located at an outer surface of the eyeball, the intra-ocular implant and the extra-ocular implant being connected by a wire connection.

2. The retinal implant device according to claim 1, wherein the functional unit comprises a processor.

3. The retinal implant device according to claim 1, wherein the functional unit comprises a photosensor adapted for detecting incident light, whereby the microelectronics element is adapted to function as an optical receiver element.

4. The retinal implant device according to claim 3, wherein the photosensor is adapted for converting a modulated light signal into a corresponding detection signal.

5. The retinal implant device according to claim 3, wherein the photosensor is adapted for receiving and detecting an infrared light signal.

6. The retinal implant device according claim 3 wherein the photosensor comprises a photodiode.

7. The retinal implant device according to claim 3, further comprising a capacitor connected to a terminal of the photosensor, wherein the capacitor is adapted for decoupling an alternating component of a detection signal from the terminal of the photosensor.

8. The retinal implant device according to claim 3, further comprising an ambient light control circuit integrated on the common semiconductor substrate and adapted for determining an ambient light intensity.

9. The retinal implant device according to claim 8, wherein the ambient light control circuit is adapted for controlling operation of the photosensor in dependence on the determined ambient light intensity.

10. The retinal implant device according to claim 3, further comprising an amplifier integrated on the common semiconductor substrate and adapted for amplifying a detection signal detected by the photosensor, or a signal derived therefrom.

11. The retinal implant device according to claim 10, wherein the ambient light control circuit comprises an automatic gain control adapted for controlling the amplifier's gain in dependence on the amplitude of the detection signal or the signal derived therefrom.

12. The retinal implant device according to claim 11, wherein the ambient light control circuit is adapted for activating amplification of the detection signal, or of the signal derived therefrom, when ambient light intensity exceeds a predefined threshold.

13. The retinal implant device according to claim 1, further comprising a capacitor integrated on the common semiconductor substrate and connected to a terminal of said functional unit, wherein the capacitor is adapted for decoupling an alternating component of a signal from the functional unit.

14. The retinal implant device according to claim 1, further comprising an amplifier integrated on the common semiconductor substrate and adapted for amplifying a signal output from the functional unit, or a signal derived therefrom.

15. The retinal implant device according to claim 1, further comprising:
    corrosion suppression means for inhibiting electrolytic corrosion of the microelectronics element in an aqueous environment.

16. The retinal implant device according to claim 1, further comprising an optical receiver element, wherein the optical receiver element is adapted for receiving and detecting a modulated light signal.

17. The retinal implant device according to claim 16,
    wherein the optical receiver element is adapted for receiving a modulated light signal carrying image information and for converting the modulated light signal into a corresponding detection signal; and/or
    wherein the optical receiver element is adapted for receiving and detecting a modulated infrared signal.

18. The retinal implant device according to claim 16, further comprising:
    an array of micro-contacts located on the retina, the micro-contacts being adapted for electrically contacting ganglia of the retina tissue; and/or
    a retina stimulation chip adapted for converting image information into corresponding stimulation impulses for the array of micro-contacts; and/or
    a high frequency receiver coil adapted for receiving a high frequency signal and for supplying an AC supply voltage to the microelectronics element and to the retina stimulation chip.

19. The retinal device according to claim 16, further comprising a photosensor adapted for supplying a detection signal to the retina stimulation chip.

* * * * *